(12) United States Patent
Arth et al.

(10) Patent No.: US 6,783,769 B1
(45) Date of Patent: Aug. 31, 2004

(54) TRANSDERMAL THERAPEUTIC SYSTEM TTS CONTAINING TOLTERODINE

(75) Inventors: Christoph Arth, Düsseldorf (DE); Claus Meese, Monheim (DE); Dietrich Wilhelm Schacht, Köln (DE); Hans-Michael Wolff, Monheim (DE)

(73) Assignee: Schwarz Pharma AG, Monheim (DE)

( * ) Notice: Subject to any disclaimer, the term of this patent is extended or adjusted under 35 U.S.C. 154(b) by 0 days.

(21) Appl. No.: 10/009,644

(22) PCT Filed: May 16, 2000

(86) PCT No.: PCT/EP00/04360

§ 371 (c)(1),
(2), (4) Date: Apr. 25, 2000

(87) PCT Pub. No.: WO00/69421

PCT Pub. Date: Nov. 23, 2000

(30) Foreign Application Priority Data

May 18, 1999 (DE) .......................... 199 22 662

(51) Int. Cl.⁷ .................. A61F 13/00; A61F 13/02; A61K 9/14; A61L 15/16
(52) U.S. Cl. ................ 424/449; 424/443; 424/484; 424/487; 424/448
(58) Field of Search ................ 424/449, 443, 424/484, 487, 448

(56) References Cited

U.S. PATENT DOCUMENTS 5,730,999 A * 3/1998 Lehmann et al. .......... 424/443

FOREIGN PATENT DOCUMENTS

| DE | 19622 902 C2 | 12/1996 |
| DE | 196 53 606 A1 | 6/1998 |
| WO | WO 98/03067 | 1/1998 |
| WO | WO 00/12069 | 3/2000 |
| WO | WO 00/12070 | 3/2000 |

* cited by examiner

Primary Examiner—Thurman K. Page
Assistant Examiner—Isis Ghali
(74) Attorney, Agent, or Firm—Peter F. Corless; Christine C. O'Day; Edwards & Angell, LLP

(57) ABSTRACT

The invention relates to a transdermal therapeutic system (TTS) for transcutaneously administering tolterodine over a period of several days and to a method for producing the same. The TTS contains a self-adhesive layer-shaped matrix composition which contains a (meth)acrylate copolymer comprising ammonium groups. The TTS also contains at least one plasticizer and up to 25 wt, % of tolterodine.

7 Claims, No Drawings

TRANSDERMAL THERAPEUTIC SYSTEM TTS CONTAINING TOLTERODINE

BACKGROUND OF THE INVENTION

1. Field of the Invention

The present invention relates to a transdermal therapeutic system (TTS) for the transcutaneous administration of tolterodine over several days, and to methods of producing said TTS.

2. Description of Related Art

The bioavailability of active ingredients which are administered orally is often unsatisfactory. The intravenous administration of active ingredients is frequently unpleasant and unsatisfactory for patients. In the bile duct, the hepatic metabolisation of many active ingredients can result in undesirable concentration ratios, toxic by-products and in a reduction of efficacy, or even in a loss of efficacy. Compared with oral administration, transdermal administration of active ingredients has various advantages. The supply of active ingredient can be better controlled over a longer period, whereby high blood level fluctuations are avoided. Moreover, the requisite therapeutically effective dose can usually be considerably reduced. Furthermore, patients often prefer a patch to pills which have to be taken once or many times a day.

In the past, there has been a multiplicity of transdermal therapeutic systems (TTS) of different structures which have been proposed for different active ingredients in order to overcome the aforementioned disadvantages of the non-transdermal administration of active ingredients.

Thus the technical documents listed below describe systems for the parenteral administration of a broad multiplicity of active ingredients which react systemically or locally; these systems are based either on a controlled dose or on the overall release of active ingredient.

Examples thereof include U.S. Pat. Nos. 3,598,122A; 3,598,123A, 3,731,683A, 3,797,494A; 4,031,894A; 4,201,211 A; 4,286,592 A; 4,314,557 A; 4,379,454 A: 4,435,180 A; 4,559,222 A; 4,568,343 A; 4,573,995 A, 4,588,580 A; 4,645,502 A; 4,702,282 A; 4,788,062 A; 4,816,258 A; 4,849,226 A; 4,908,027 A: 4,943,435 A and 5,004,610 A.

In the late sixties of this century, however, it was initially assumed, based on theoretical considerations, that any active ingredient exhibiting a short half-life, high efficacy and good permeation through the skin was suitable for reliable and effective administration by means of a TTS. However, it was not possible to realise these initial expectations regarding the possibility of the transdermal administration of active ingredients by means of a TTS. The reason for this is mainly that skin has been provided by nature with a variety of insuperable qualities in order to maintain its function as an intact barrier to the ingress of extraneous substances into the body (in this respect, see: Transdermal Drug Delivery: Problems and Possibilities, B. M. Knepp et al., CRC Critical Review and Therapeutic Drug Carrier Systems, Vol. 4, Issue 1 (1987)).

Therefore, transdermal administration is available only for those few active ingredients which comprise a suitable combination of many favourable characteristics. The requisite characteristics, which ensure reliable and effective transdermal administration, cannot be predicted for a given substance, however.

The requirements imposed on an active ingredient which is suitable for transdermal administration are:

capable of passing through the skin, no impairment of the adhesive capacity of the patch by the active ingredient, avoidance of skin irritation, avoidance of allergic reactions, favourable pharmacokinetic properties, favourable pharmacodynamic properties, a relatively wide therapeutic window, metabolic properties which are consistent with therapeutic use comprising continuous delivery.

The above list of requirements is undoubtedly not exhaustive. So that an active ingredient can be available for transdermal administration, the "correct" combination all of these requirements is desirable.

The aforementioned requirements for the active ingredient apply similarly to the TTS composition which contains the respective active ingredient and the nature of the structure thereof.

Transdermal therapeutic systems (TTS) are usually patches which are provided with an impermeable outer layer, a peelable protective layer and a matrix which contains an active ingredient, or a reservoir which contains an active ingredient and comprises a semipermeable membrane. In the first case these are termed matrix patches, and in the second case they are termed membrane systems.

The substances used for the outer layer are usually polyesters, polypropylene, polyethylene, polyurethane etc., which can also be metallised or pigmented. Suitable substances for the peelable protective layer include polyesters, polypropylene and also paper with a silicone and/or polyethylene coating. Fluoropolymers are also used.

A multiplicity of substances, such as those based on polyacrylate, silicones, polyisobutylene, butyl rubber, styrene/butadiene copolymers or styrene/isoprene copolymers, can be used as the matrix which contains the active ingredient.

The membranes which are used in membrane systems can be microporous or semipermeable, and are usually based on an inert polymer, particularly polypropylene, polyvinyl acetate or silicones.

Whereas matrix compositions which contain an active ingredient can be self-adhesive, matrix compositions which contain an active ingredient but which are not self-adhesive can also be used depending on the active ingredient used, but the structure of the patch or TTS consequently has to be provided with an overtape.

To ensure the requisite flux of active ingredient, skin penetration enhancers are frequently necessary as additives, such as aliphatic, cycloaliphatic and/or aromatic-aliphatic alcohols, each of which is monohydric or polyhydric and contains up to 8 C atoms, alcohol/water mixtures, saturated and/or unsaturated fatty alcohols which each contain 8 to 18 carbon atoms, saturated and/or unsaturated fatty acids which each contain 8 to 18 carbon atoms and/or esters thereof, as well as vitamins.

Moreover, stabilisers such as polyvinyl pyrrolidone, α-tocopherol succinate, propyl gallate, methionine, cysteine and/or cysteine hydrochloride are frequently added to the matrix which contains the active ingredient.

As shown by the above statements, numerous TTS structures and materials which are used therefor are known. However many interacting requirements have to be taken into account if a drug in form of a TTS is to satisfy a medical need.

The following problems have to be taken into account during the development of a TTS containing an active ingredient:

1. The permeability of the skin to the active ingredient may be too low to achieve the therapeutically necessary rate of penetration, and/or the delay time ("lag-time") until the therapeutically necessary plasma level is reached is too long, with the consequence that additives which increase the rate of penetration through the skin have to be administered.
2. The polymer matrix which contains the active ingredient, and which optionally contains skin penetration enhancers in addition, may not be physically stable over an extended period of storage. In particular, recrystallisation of the active ingredient may occur, which results in an uncontrollable decrease in the capacity of the TTS to release active ingredient.
3. For self-adhesive polymer films, a high content of active ingredient and/or of skin penetration enhancers in the polymeric backing material makes it difficult to achieve the optimum adhesive properties for the transdermal system.
4. For applications comprising several days of administration, the rate of resorption of the active ingredient decreases in an unacceptable manner, so that additional control layers and/or control components are necessary.
5. Furthermore, it is known from the literature that the fatty acid esters of polyhydric alcohols which are frequently used to promote penetration through the skin contain impure blending agents of variable quality. This results in increases in penetration which exhibit poor reproducibility (Burkoth et al. 1996, DE 196 22 902 A1).

The problems described above have therefore given rise to a multiplicity of designs of transdermal therapeutic systems, which are reflected in the prior art in this field.

DE 196 53 606 A1 describes an adhesive and bonding agent for a TTS comprising defined quantitative proportions of the components a), a (meth)acrylate polymer which may contain quaternary ammonium groups, b) an organic di- or tricarboxylic acid, and c), a plasticiser, which can be a triester of citric acid.

As shown by the above statements, many patch structures are known, as are the materials used therefor. Nevertheless, for many active ingredients which are processed to form transdermal therapeutic systems there has hitherto been a considerable need for TTS systems which facilitate the release of active ingredient as required by the therapy concerned without involving costly structures, and which comprise the optimum relationships with regard to their constituents overall. This also applies to the active ingredient tolterodine if this is to be administered transcutaneously.

Tolterodine is the international non-proprietary name (INN) for the R-isomer of N,N-diisopropyl-3-(2-hydroxy-5-methylphenyl)-3-phenylpropylamine (IUPAC description: (+)-(R)-2-(α[2-(diisopropylamino)ethyl]benzyl)4-methylphenol)). The term "tolterodine" is employed hereinafter to mean N,N-diisopropyl-3-(2-hydroxy-5-ethylphenyl)-3-phenylpropylamine. Inasmuch as reference is made to the individual isomers, namely the R- or S-isomer or a racemic mixture of the R- and S-isomers, these are referred to as R-, S- and R,S-tolterodine, respectively.

Tolterodine is used therapeutically for the treatment of bladder instability associated with the symptoms of involuntary discharge of urine, pollakiuria and urinary incontinence. The recommended dose is 2 mg of tolterodine twice daily, and is administered orally.

After oral application, tolterodine is metabolised to very different degrees in the bile duct. Thus the absolute bioavailability of tolterodine is 65% for slow metabolisers, but is only 17% for rapid metabolisers. Since even the resulting 5-hydroxymethyl metabolite is pharmacologically active, the reduced tolterodine blood level does not result in any loss of efficacy with rapid metabolisers. Nevertheless, it is desirable that fluctuations such as these between individuals are avoided and that differences in efficacy which result therefrom are avoided. Moreover, different plasma levels occur if tolterodine is administered with or without the ingestion of food. In principle, these problems can be avoided by the transdermal administration of tolterodine, since the active ingredient is then supplied directly to the blood circulation without passing through the gastrointestinal tract and the bile duct. The plasma fluctuations comprising high concentration peaks which occur with oral administration, and which result in undesirable side-effects such as dry mouth, dyspepsia, sickness, accommodation problems and confusion, can be avoided by transdermal administration. Similarly, levels of active ingredient which decrease below the threshold of efficacy, and the involuntary, round the clock discharge of urine can be avoided. Furthermore, the liver is subjected to considerably less loading by the active ingredient due to the avoidance of the bile duct, which is especially desirable for patients with a pre-damaged liver, such as patients with cirrhosis of the liver, for example.

WO 98/03067 A1 teaches the use of S-tolterodine for the treatment of bladder voiding disorders, including incontinence. Amongst other methods, transdermal application is also proposed there for the administration of the active ingredient. However, the aforementioned patent contains no technical teaching on the implementation of transdermal application and does not contain an example which relates thereto.

DETAILED DESCRIPTION OF THE INVENTION

Transdermal therapeutic systems for the administration of tolterodine are not described in the prior art.

The object of the present invention is therefore to provide a TTS for tolterodine. The TTS should be of simple structure, should exhibit good compatibility with the skin, should be physically and chemically stable over extended periods of storage, should possess good properties of adhesion, and should release as much active ingredient per unit area as possible, both on and through the skin.

This object has been achieved by providing a transdermal therapeutic system (TTS) for the transcutaneous administration of tolterodine which contains a self-adhesive matrix material in the form of a layer, which layer contains a (meth)acrylate copolymer comprising ammonium groups, at least one plasticiser, and up to 25% by weight tolterodine. Surprisingly, tolterodine is released on and through the skin therefrom at a high rate of release which for other active ingredients is only known in combination with skin penetration enhancers. Consequently, the dose which is therapeutically necessary can be administered using a TTS with a small release surface, without having to accept an increased risk of skin irritation due to skin penetration enhancers.

In the sense of the present invention, the terms "several days" and "solid solution" are to be understood as follows:
a) "several days": for therapeutic use, the TTS can be applied to the skin for a period of from 1 to 7 days, preferably from 1 to 4 days.
b) "solid solution": the pharmaceutical active ingredient is distributed in the form of dispersed molecules in the TTS matrix.

According to another embodiment of the invention, the TTS systems described above can be additionally surrounded on the skin, with the exception of the release surface of the matrix which contains tolterodine, by a larger dermal plaster which is free from active ingredient, for fixing to the skin at the point of application (overtape).

This structure results in the advantage that different skin types and climatic zones can be taken into account. Moreover, firstly the co-adhesion/adhesion properties, and secondly the solubility, rate of dissolution and release properties of the active ingredient, can be optimised substantially independently of each other.

The matrix which contains the active ingredient preferably contains (R,S)-tolterodine or R-tolterodine.

According to another embodiment of the invention, the matrix material contains deuterated tolterodine as an active ingredient. Deuterated tolterodine is obtained by replacing one or more hydrogen atoms by deuterium, which is an isotope thereof. In principle, any hydrogen atom which the tolterodine contains can be replaced by deuterium. The methyl substituent of the aromatic moiety, or the aromatic moiety itself, preferably contains at least one deuterium atom.

An example thereof is 2-(3-diisopropylamino-1-phenylpropyl)-4-[$^2$H$_3$]methyl-phenol.

It has surprisingly been found that the rate of dermal penetration of deuterated tolterodine is considerably increased compared with that of non-deuterated tolterodine, which exhibits a very high rate of dermal penetration anyway.

According to a further embodiment, the matrix material preferably contains 10–20% by weight of tolterodine.

Finally, the matrix material which contains an active ingredient can be a solid solution.

The formation of a solid solution of tolterodine in the (meth)acrylate polymer which contains ammonium groups could not have been anticipated, and is all the more surprising because many active ingredients do not form solid solutions (comprising a distribution of dispersed molecules) in polymers, but are incorporated in the form of solid particles in the polymer concerned, as can be identified by electron microscopy. In contrast to solid solutions, crystalline materials also exhibit a Debye-Scherrer pattern.

According to another embodiment of the invention, the matrix material which contains tolterodine contains at least one triester of citric acid. The triester of citric acid preferably contains short chain alkanoic acids, particularly suitable examples of which include methanoic acid, ethanoic acid, n-propanoic acid, i-propanoic acid, n-butanoic acid, sec.-butanoic acid and tert.-butanoic acid.

In one preferred embodiment, the matrix material which contains tolterodine contains n-butyl citrate, ethyl citrate or a mixture thereof.

Based on the composition according to the invention and to the structural form of the TTS, it is surprising that satisfactory physical stability of the system is ensured on long-term storage, despite high concentrations of active ingredient in the polymer matrix.

It could not have been anticipated that the polymer which is used as the polymer matrix which contains the active ingredient, after being adhesively bonded to the skin, would result in intimate contact between the matrix material and the skin, of a quality such that a TTS is formed which is self-adhesive for several days and which satisfies both therapeutic and economic requirements, particularly those requirements related to commercial economics.

At the same time, patient compliance is taken into account to a very considerable extent.

If the embodiment comprising a dermal patch which is free from active ingredient and an overtape is selected, it is only necessary to employ dermal patches of small area which comprise an adhesive edge only a few mm wide.

This is both economic and is an advantage with regard to patient compliance.

According to another embodiment of the invention, the backing film of the TTS comprises a metallised coating or oxide coating on its matrix side.

The structure of the TTS according to the invention is illustrated in drawings 1 and 2.

Drawing 1 shows the embodiment without an overtape, consisting of a polymer matrix (1) which contains an active ingredient, a removable protective film (5) and a covering film (2).

Drawing 2 shows the embodiment which does comprise an overtape. In addition to the layers which are contained in the embodiment illustrated in drawing 1, it contains an overtape comprising a backing film (4) and an adhesive film (3).

The, TTS according to the invention can be produced by what is termed the "solvent-based process". For this purpose, the polymer, active ingredient and the other constituents are dissolved in a common solvent and the solution obtained is distributed as a thin layer on a support. The coated support is dried in order to remove the solvent contained in the polymer matrix, is covered by a further film and is finally separated into pieces of the desired size.

Alternatively, the TTS can also be produced by what is termed the "hot melt process". For this purpose, the polymer is melted and mixed with the active ingredient and with the other auxiliary materials, and the mixture obtained is distributed as a thin layer on a support (=removable protective film) and is allowed to cool. It is covered with another film (covering film) and is separated into pieces of the desired size.

The matrix which contains tolterodine is preferably produced by melt extrusion, wherein the active constituent is continuously metered, as a solid substance, into a melt comprising a polymer and a plasticiser, and the polymer melt which is obtained, and which contains the active ingredient, is continuously coated, immediately the active ingredient has been added, on to a removable protective layer as a coat of thickness ranging from 0.02 to 0.5 mm, and the double layer laminate which is obtained is provided with an outer layer on the other side of the matrix. The matrix material which contains the active ingredient is preferably produced and further processed in one continuous, cost-saving operation comprising short processing times. Thermal loading of the polymer material which contains the active ingredient is reduced to a minimum, so that decomposition reactions are prevented.

The invention is explained with reference to the following examples:

EXAMPLE 1

2.52 g Eudragit RS 100, (=poly(ethyl acrylate, methyl methacrylate, trimethylammonio-ethyl methacrylate chloride), with a molar ratio of monomer units of 1:2:0.1), 1.16 g tributyl citrate, and 0.65 g R-tolterodine, were dissolved in a glass beaker with stirring, with the addition of 8.00 g ethyl acetate.

The polymer solution which was obtained was spread, using a doctor blade, on to a peelable polyester film (=backing film) of thickness about 100 µm which had been metallised with aluminium and provided with a silicone coating on both sides, and was dried for 30 minutes at 45° C. in a recirculating air oven, so that a polymer film which contained tolterodine was obtained which had a weight per unit area of 110 g/m². The latter was subsequently covered with a polyester film of thickness about 19 µm. Transdermal systems (TTS) of size 5 cm² were punched out from the 3-layer laminate which was thus obtained, and consisted of a peelable protective layer, a polymer film containing the active ingredient and a covering film.

Tolterodine Flux Measurements in Vitro

Flux Measurements Through Mouse Skin

A TTS with a punched-out area of 2.55 cm² was fixed to the epidermal side of skin from the stomach and back of hairless mice in a horizontal diffusion cell. Immediately thereafter, the acceptor chamber of the cell was filled, free from air bubbles, with a phosphate buffer solution (0.066 molar) at pH 6.2, which had been preheated to 32° C., and the release medium was maintained at a controlled temperature of 32±0.5° C. using a thermostat.

When samples were taken (after 3, 6, 24, 30, 48, 54 and 72 hours), the medium was replaced by fresh medium at a controlled temperature of 32±0.5° C.

Flux Measurements Through Human Skin

Testing was performed in a flow cell as described by Tiemessen (Harry L. G. M. Thiemessen et al., Acta Pharm. Technol. 34 (1988), 99–101), on freshly prepared, human skin approximately 200 µm thick, which rested on a silicone membrane facing the acceptor cell (acceptor medium: phosphate buffer solution, 0.066 molar, pH 6.2; at a controlled temperature of 32±0.5° C.

Samples were taken after 3, 6, 9, 12, 15, 18, 21, 24, 27, 30, 33, 36, 39, 42, 45, 48, 51, 54, 57, 60, 63, 66, 69 and 72 hours.

In these tests on human skin, the content of R-tolterodine base in the release- and acceptor medium was determined by high-performance liquid chromatography under the following conditions: stationary phase: $C_8$ inversion phase, 3.9×150 mm, 5 µm; column temperature=room temperature; eluent: 700 parts by volume of sodium dihydrogen phosphate buffer (0.05 mol), pH 3.0, 300 parts by volume of acetonitrile; Detection: UV at 220 nm; flow rate: 1.2 ml/min, injection volume: 50 µl at 15° C.

The test results for Example 1 are presented in Table 1

TABLE 1

Flow rates of R-tolterodine base through an excised skin preparation (Example 1) Ch.-B. INZ 006)

| | Content of R-tolterodine base | Mean cumulative flux [µg/cm²] after | | |
|---|---|---|---|---|
| | [% by weight] | 24 hours | 48 hours | 72 hours |
| Mouse skin (n = 4) | 15.0 | 524.2 | 849.0 | 1036.4 |
| Human skin (n = 3) | 15.0 | 130.5 | 460.1 | 731.0 |

EXAMPLE 2

9.71 g Eudragit. RS 100, (=poly(ethyl acrylate, methyl methacrylate, trimethylammonio-ethyl methacrylate chloride), with a molar ratio of monomer units of 1:2:0.1), 4.76 g tributyl citrate, and 2.50 g (R,S)-tolterodine were dissolved in a glass beaker with stirring, with the addition of 32.00 g ethyl acetate.

The polymer solution which was obtained was spread, using a doctor blade, on to a peelable polyester film (=backing film) of thickness about 100 µm which had been metallised with aluminium and provided with a silicone coating on both sides, and was dried for 30 minutes at 45° C. in a recirculating air oven, so that a polymer film which contained tolterodine was obtained which had a weight per unit area of 125 g/m². The latter was subsequently covered with a polyester film of thickness about 19 µm (=covering film). Transdermal systems (TTS) of size 5 cm² were punched out from the 3-layer laminate which was thus obtained, and consisted of a peelable protective layer, a polymer film containing the active ingredient, and a covering film.

Tolterodine Flux Measurements in Vitro

Flux Measurements Through Mouse Skin

A TTS with a punched-out area of 2.55 cm² was fixed to the epidermal side of skin from the stomach and back hairless mice in a horizontal diffusion cell. Immediately thereafter, the acceptor chamber of the cell was filled, free from air bubbles, with a phosphate buffer solution (0.066 molar) at pH 6.2, which had been preheated to 32° C., and the release medium was maintained at a controlled temperature of 32±0.5° C. using a thermostat.

When samples were taken (after 3, 6, 24, 30, 48, 54 and 72 hours), the medium was replaced by fresh medium at a controlled temperature of 32±0.5° C.

Flux Measurements Through Human Skin

Testing was performed in a flow cell as described by Tiemessen (Harry L. G. M. Thiemessen et al., Acta Pharm. Technol. 34 (1988), 99–101), on freshly prepared, human skin approximately 200 µm thick, which rested on a silicone membrane facing the acceptor cell (acceptor medium: phosphate buffer solution, 0.066 molar, pH 6.2; at a controlled temperature of 32±0.5° C.

Samples were taken after 3, 6, 9, 12, 15, 18, 21, 24, 27, 30, 33, 36, 39, 42, 45, 48, 51, 54, 57, 60, 63, 66, 69 and 72 hours.

In these tests on human skin, the content of (R,S)-tolterodine base in the release- and acceptor medium was determined by high-performance liquid chromatography under the following conditions: stationary phase: $C_8$ inversion phase, 3.9×150 mm, 5 µm; column temperature=room temperature; eluent: 700 parts by volume of sodium dihydrogen phosphate buffer (0.05 mol), pH 3.0, 300 parts by volume of acetonitrile; Detection: UV at 220 nm; flow rate: 1.2 ml/min, injection volume: 50 µl at 15° C.

The test results for Example 2 are presented in Table 2

TABLE 2

Flow rates of (R,S)-tolterodine base through an excised skin preparation (Example 2) Ch.-B. INZ 007)

| | Content of (R,S)-tolterodine base | Mean cumulative flux [µg/cm²] after | | |
|---|---|---|---|---|
| | [% by weight] | 24 hours | 48 hours | 72 hours |
| Mouse skin (n = 4) | 15.0 | 648.8 | 1110.4 | 1302.0 |
| Human skin (n = 3) | 15.0 | 208.4 | 718.9 | 1219.4 |

EXAMPLE 3

9.71 g Eudragit RS 100, (=poly(ethyl acrylate, methyl methacrylate, trimethylammonioethyl methacrylate chloride), with a molar ratio of monomer units of 1:2:0.1), 4.76 g tributyl citrate, and 2.50 g R-(+)-2-(3-diisopropylarnino-1-phenyl-propyl)-4-[$^2$H$_3$]methylphenol(R-D$_3$)-tolterodine) were dissolved in a glass beaker with stirring, with the addition of 32.00 g ethyl acetate.

The polymer solution which was obtained was spread, using a doctor blade, on to a peelable polyester film (=backing film) of thickness about 100 μm which had been metallised with aluminium and provided with a silicone coating on both sides, and was dried for 30 minutes at 45° C. in a recirculating air oven, so that a polymer film which contained tolterodine was obtained which had a weight per unit area of 125 g/m$^2$. The latter was subsequently covered with a polyester film of thickness about 19 μm. Transdermal systems (TTS) of size 5 cm$^2$ were punched out from the 3-layer laminate which was thus obtained, and consisted of a peelable protective layer, a polymer film containing the active ingredient and a covering film.

Tolterodine Flux Measurements in Vitro
Flux Measurements Through Mouse Skin

A TTS with a punched-out area of 2.55 cm$^2$ was fixed to the epidermal side of skin from the stomach and back hairless mice in a horizontal diffusion cell. Immediately thereafter, the acceptor chamber of the cell was filled, free from air bubbles, with a phosphate buffer solution (0.066 molar) at pH 6.2, which had been preheated to 32° C., and the release medium was maintained at a controlled temperature of 32±0.5° C. using a thermostat.

When samples were taken (after 3, 6, 24, 30, 48, 54 and 72 hours), the medium was replaced by fresh medium at a controlled temperature of 32±0.5° C.

In these tests on mouse skin, the content of R-(D$_3$)-tolterodine base in the release- and acceptor medium was determined by high-performance liquid chromatography under the following conditions: stationary phase: C$_8$ inversion phase, 3.9×150 mm, 5 μm; column temperature=room temperature; eluent: 700 parts by volume of sodium dihydrogen phosphate buffer (0.05 mol), pH 3.0, 300 parts by volume of acetonitrile; Detection: UV at 220 nm; flow rate: 1.2 ml/min, injection volume: 50 μl at 15° C.

Flux Measurements Through Human Skin

Testing was performed in a flow cell as described by Tiemessen (Harry L. G. M. Thiemessen et al., Acta Pharm. Technol. 34 (1988), 99–101), on freshly prepared, human skin approximately 200 μm thick, which rested on a silicone membrane facing the acceptor cell (acceptor medium: phosphate buffer solution, 0.066 molar, pH 6.2; at a controlled temperature of 32±0.5° C.

Samples were taken after 3, 6, 9, 12, 15, 18, 21, 24, 27, 30, 33, 36, 39, 42, 45, 48, 51, 54, 57, 60, 63, 66, 69 and 72 hours.

In these tests on human skin, the content of R-(D$_3$)-tolterodine base in the release- and acceptor medium was determined by high-performance liquid chromatography under the following conditions: stationary phase: C$_8$ inversion phase, 3.9×150 mm, 5 μm; column temperature=room temperature; eluent: 700 parts by volume of sodium dihydrogen phosphate buffer (0.05 mol), pH 3.0, 300 parts by volume of acetonitrile; Detection: UV at 220 nm; flow rate: 1.2 ml/min, injection volume: 50 μl at 15° C.

The test results for Example 3 are presented in Table 3

TABLE 3

Flow rates of R-(D$_3$)-tolterodine base through excised skin preparation (Example 3) Ch.-B. INZ 013)

| | Content of (R,S)-tolterodine base | Mean cumulative flux [μg/cm$^2$] after | | |
|---|---|---|---|---|
| | [% by weight] | 24 hours | 48 hours | 72 hours |
| Mouse skin (n = 4) | 15.0 | 872.0 | 1388.4 | 1737.4 |
| Human skin (n = 3) | 15.0 | 165.9 | 490.8 | 784.2 |

What is claimed is:

1. A transdermal therapeutic system (TTS) for transcutaneous administration of tolterodine over a period of up to seven days, wherein the system comprises a layer of a tolterodine containing a matrix composition disposed on a carrier film, said matrix composition comprising a solid solution of (a) a copolymer of ethyl acrylate and methyl methacrylate containing about 5% trimethylammonium ethyl methacrylate chloride as the sole (meth)acrylate copolymer, (b) at least one plasticizer and (c) up to 25 weight percent of tolterodine, and wherein the system is free of an adhesive layer.

2. A transdermal therapeutic system for the transcutaneous administration of tolterodine over a period of up to seven days, wherein the system comprises a layer form of a tolterodine-containing matrix composition disposed on a carrier film, said matrix composition comprising (a) a copolymer of ethyl acrylate and methyl methacrylate containing about 5% trimethylammonium ethyl methacrylate chloride as the sole (meth)acrylate copolymer, (b) at least one plasticizer, and (c) up to 25 weight percent of tolterodine, and that said matrix composition, with the exception of its release surface, is surrounded by a larger patch, which is free from active ingredient, for fixing to skin at the point of application.

3. A TTS according to any one of claims 1–2, characterized in that the matrix composition which contains an active ingredient contains (R,S)-tolterodine or R-tolterodine.

4. A TTS according to any one of claims 1–2, characterized in that the matrix composition which contains an active ingredient contains deuterated tolterodine.

5. A TTS according to any one of claims 1–2, characterized in that the matrix composition which contains an active ingredient contains at least one triester of citric acid as the plasticizer.

6. A TTS according to claim 5, characterized in that it contains tributyl citrate, on its own or in admixture with triethyl citrate, as the plasticizer.

7. A TTS according to any one of claims 1–2, characterized in that the carrier film comprises a metallised or oxide coating on its matrix side.

* * * * *

UNITED STATES PATENT AND TRADEMARK OFFICE
CERTIFICATE OF CORRECTION

PATENT NO. : 6,783,769 B1 Page 1 of 1
DATED : August 31, 2004
INVENTOR(S) : C. Arth et al.

It is certified that error appears in the above-identified patent and that said Letters Patent is hereby corrected as shown below:

Title page,
Item [86], §371 (c)(1), (2), (4) Date, please correct "Apr. 25, 2000" to
-- Apr. 25, 2002 --
Item [30], Foreign Appliaction Priority Data, please correct "199 22 662" to
-- 199 22 662.8 --
Item [57], ABSTRACT,
Line 7, please correct "25 wt, %" to -- 25 wt. % --

Column 3,
Line 59, please correct "racernic" to -- racemic --

Column 6,
Line 21, please correct "The, TTS" to -- The TTS --

Column 7,
Line 61, please correct "Eudragit." to -- Eudragit --

Column 9,
Line 2, please correct "diisopropylarnino" to -- diisopropylamino--

Signed and Sealed this

Ninth Day of August, 2005

JON W. DUDAS
*Director of the United States Patent and Trademark Office*